(12) United States Patent
Pattikonda et al.

(10) Patent No.: US 6,246,788 B1
(45) Date of Patent: Jun. 12, 2001

(54) SYSTEM AND METHOD OF OPTICALLY INSPECTING MANUFACTURED DEVICES

(75) Inventors: Ramakrishna Pattikonda; Youling Lin, both of Dallas; Kathleen Hennessey, Lubbock, all of TX (US)

(73) Assignee: ISOA, Inc., Richardson, TX (US)

( * ) Notice: Subject to any disclaimer, the term of this patent is extended or adjusted under 35 U.S.C. 154(b) by 0 days.

(21) Appl. No.: 09/074,301

(22) Filed: May 6, 1998

Related U.S. Application Data

(63) Continuation-in-part of application No. 08/867,156, filed on May 30, 1997, now Pat. No. 6,091,846.
(60) Provisional application No. 60/053,090, filed on Jul. 3, 1997.

(51) Int. Cl.[7] .................................................. G06K 9/00
(52) U.S. Cl. ............................................ 382/147; 382/149
(58) Field of Search .................................... 382/145, 147, 382/149, 151, 218, 224; 348/86, 87, 94, 126

(56) References Cited

U.S. PATENT DOCUMENTS

| | | | |
|---|---|---|---|
| 5,015,097 | * 5/1991 | Nomoto et al. | 356/314 |
| 5,515,453 | * 5/1996 | Hennessey et al. | 382/141 |
| 5,696,835 | * 12/1997 | Hennessey et al. | 382/141 |
| 6,014,461 | * 1/2000 | Hennessey et al. | 382/224 |

OTHER PUBLICATIONS

Ching et al. "Concurrent Acquisition and Processing of Multi-spectral Shadow Information for 3D Computer Vision". Proceedings of IECON '93. vol. 3, Nov. 1993, pp. 1736–1741.*

* cited by examiner

Primary Examiner—Bhavesh Mehta
(74) Attorney, Agent, or Firm—Smith, Danamraj & Youst, P.C.

(57) ABSTRACT

An apparatus, system, and method of optically inspecting printed circuit boards (PCBs) for defects, that reliably determines the dimensions of components including those having the same color as the background, and which can detect components which are missing, misoriented, misaligned, or not properly seated. The apparatus uses a camera and a coherent primary light source mounted at an angle away from the vertical so as to produce sharply defined PCB component shadows on the top surface of the PCB. An image of the PCB is captured, the shadow edges are symbolically decomposed into primitives from which gradients are produced, and then compared to a previously captured gradient of a defect-free PCB. Differences in the two image gradients, if any, are used to identify missing, misaligned, misoriented, and improperly seated components, and to detect foreign objects and other PCB defects.

33 Claims, 6 Drawing Sheets

SYSTEM AND METHOD OF OPTICALLY INSPECTING MANUFACTURED DEVICES

PRIORITY STATEMENT UNDER 35 U.S.C. § 119 and 37 C.F.R. § 1.78

This nonprovisional application claims priority based on the prior U.S. Provisional Pat. Application Ser. No. 60/053,090, filed July 3, 1997, entitled "System and Method of Optically Inspecting Manufactured Devices", and a continuation-in-part of U.S. patent application Ser. No. 08/867,156, filed May 30, 1997, now U.S. Pat. No. 6,091,846, entitled "System and Method for Anomaly Detection". Both of these prior applications, in their entirety, are incorporated herein by reference.

BACKGROUND OF THE INVENTION

1. Technical Field of the Invention

The present invention relates to the inspection of manufactured devices and, more specifically, to an apparatus, system, and method for optically inspecting Printed Circuit Boards (PCBs) for manufacturing defects such as missing components, misplaced components, skewed components, and foreign objects.

2. Description of Related Art

Printed Circuit Boards (PCBs) are typically constructed from a heat-resistant plastic base with selected channels cut therein for holding metallic conductors, and are usually covered with an insulative resin. PCBs simplify the construction of electronic devices such as computers, smoke detectors, stereos and other consumer electronics by providing a common support for, and the correct electrical connections between, electronic components such as resistors, capacitors, inductors, and digital devices. A manufacturer need only correctly place an appropriate electronic component on a PCB in a designated location and, because the PCB is designed to provide the appropriate electrical connections between components, practically all electrical connections required between that device, other devices or output connections are automatically made. This allows for the "wireless" construction of many electronic devices, which greatly reduces manufacturing time and practically eliminates errors commonly associated with wire connections.

In the manufacturing of PCB based devices, the PCB is populated with components either by hand or by machine, and the components are then soldered to the PCB by methods well known in the art, such as with solder machines or with surface-mount technologies. The PCB is then inspected to insure that each component was correctly placed on the PCB. One method of inspection is optical inspection.

Optical inspection devices typically employ a PCB support which holds a populated PCB under an overhead camera and multiple light sources. In operation, the optical inspection device typically lights the PCB from several directions in order to eliminate shadows, and the camera captures a gray-scale (black-and-white) image of the PCB. In a process commonly called convolution, this image is then sent to a computer which compares the image, pixel by pixel, to a stored image of a properly populated PCB. Differences between the captured image and the image of the properly constructed PCB are recorded as defects.

The existing method of optically inspecting a PCB has several disadvantages. First, when a component has the same color as the background, the component is effectively camouflaged relative to the PCB, making it difficult for the computer to determine where the edges of a component are placed and thereby provide the location of the component. This reduces the accuracy of the optical inspection since a misplaced component may not be reported as a defect. Alternatively, since the component may not be accurately traced, it may be reported as a defect even though it is correctly placed. Furthermore, since existing optical inspection devices view the components from directly above, it is difficult to determine whether components are properly seated (vertically) even when they are in a proper location. Finally, since each manufacturer may manufacture electrically identical devices or boards in different colors, when components or boards of different colors are loaded into a PCB system, prior art defect detection methods may erroneously "detect" defects when no defects are present.

Some of the aforementioned deficiencies can be overcome by using laser or X-ray imaging. However, because laser and X-ray imaging techniques illuminate and reconstruct only one point at a time, they are slow and very expensive. Alternatively, some manufactures of optical PCB inspection equipment use multiple cameras to create a "stereo" image of the PCB. Stereo imaging can detect a vertically misplaced component, but requires an additional camera and still has trouble detecting component edges when the components are the same color as the PCB. Stereo imaging also has trouble detecting small components.

In order to overcome the disadvantages of the existing methods of PCB inspection, it would be advantageous to have an apparatus, system and method of optically inspecting PCBs for manufacturing defects, such as alignment errors, missing components, embedded components, skewed components, and foreign objects. Ideally, the defect detection system should be able to reliably detect and assess the location of components having the same color as the PCB or other background, and detect when components are not properly vertically seated on the PCB. In addition, it would also be advantageous for such a system to utilize only a single camera and not require extensive lighting, thereby reducing system costs. The present invention provides such a system and method.

SUMMARY OF THE INVENTION

Provided is an inspection system for a production printed circuit board (PCB) essentially comprising a PCB, a PCB support for holding the PCB being inspected, an image capturing device located above the PCB, a device for emitting light at an angle relative to the PCB being inspected such that PCB components cast shadows upon the PCB, and a computer for comparing the shadows captured from an image of a production PCB to the shadows defined for a defect-free PCB. The PCB inspection system image capturing device is preferably an area-scan camera, but may also be a line-scan camera. The PCB inspection system may define shadow sizes and shapes for a defect-free PCB through computer aided drafting or via the image capturing device. Furthermore, the device for emitting light may emit light in infrared, ultraviolet, or any of the visible light spectra. The PCB inspection system uses production PCB shadow images to generate image grammars. The shadow grammars are decomposed and compared to shadow grammars generated for a defect-free PCB to produce PCB gradients. By comparing production gradients to gradients generated for a defect-free PCB, PCB defects are more easily detected.

Because the PCB inspection system uses shadow detection, angular light is one important feature of the invention. Thus, the PCB inspection system provides a device for emitting light at an angle of less than 90 degrees relative to the PCB. For example, the device for emitting light may be limited to emitting light between angles of 30 degrees and 60 degrees, or at an angle of about 45 degrees relative to the PCB. Under some circumstances, the device for emitting light may optimally be set at an angle of less than 30 degrees. The PCB inspection system further comprises a knowledge base for storing at least one captured image, or the features, grammars, or gradients of a captured image of a properly populated PCB.

In another aspect, the present invention provides a method of detecting defects on a production printed circuit board (PCB) which includes the steps of: shining a first light on the production PCB to generate at least one component shadow on the PCB, capturing a first image of the PCB, detecting the shadow, determining a length dimension, a width dimension, and a darkness level of the shadow to generate at least one primitive, and comparing the primitive to a predetermined correct primitive.

The method may further comprise the steps of: shining a second light on the PCB from a different direction than the first light to generate a second component shadow on the PCB and capturing a second image of the PCB. Additional primitives are generated to describe the second component shadow. Then, the primitives are stored in a knowledge base. The collection of primitives that describe a shadow is called a grammar. The grammars generated from the shadow cast by the first light and the shadow cast by the second light are then used to produce shadow edge gradients. Shadow edge gradients for a production PCB are then compared to the shadow edge gradients produced from a grammar generated for a defect-free PCB. After these gradients are compared, PCB defects are recorded and are matched with a database of known or possible PCB defects to identify the defect type.

BRIEF DESCRIPTION OF THE DRAWINGS

The invention will be better understood and its numerous objects and advantages will become more apparent to those skilled in the art by reference to the following drawings, in conjunction with the accompanying specification, in which.

DETAILED DESCRIPTION OF A PREFERRED EMBODIMENT

The present invention provides an apparatus, system and method of optically inspecting manufactured devices. In particular, the present invention optically inspects printed circuit boards (PCBs), reliably traces components having the same color as the component background, and detects components which are not properly seated by detecting and tracing component shadows. Because it detects component shadows, it provides defect detection even when component colors or PCB colors are changed. Thus, the present invention solves the problems associated with prior art optical inspection techniques by comparing production PCB gradients to defect-free PCB gradients.

Figure 1:
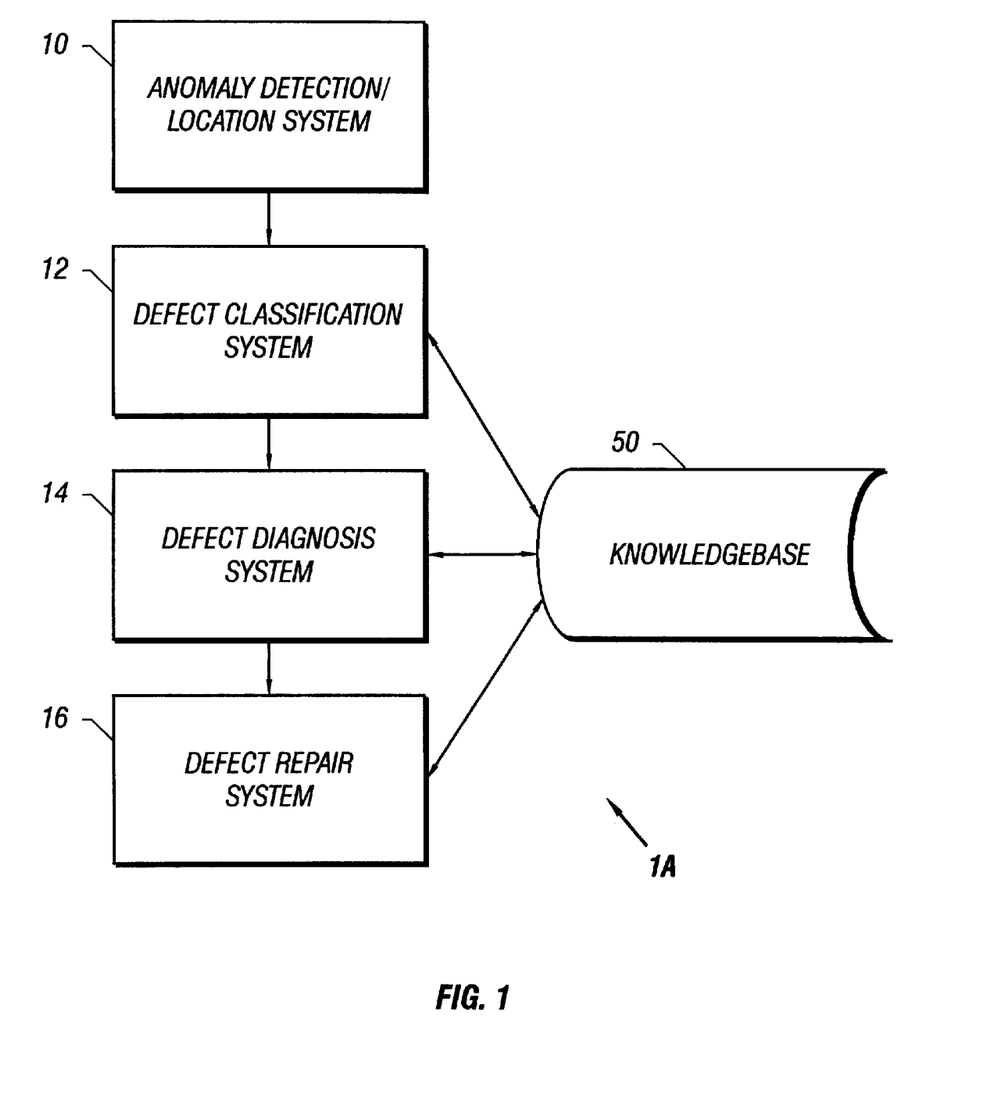
FIG. 1 is a block diagram illustrating the interrelations of systems in an anomaly detection and correction system.

FIG. 1 is a block diagram illustrating the interrelations of sub-systems in an anomaly detection and correction system 1A. In the anomaly detection and correction system 1A there is an anomaly detection/location system 10, a defect classification system 12, a defect diagnosis system 14, a defect repair system 16, and a knowledge base 50. The anomaly detection/location system 10 pinpoints the location of PCB defects. Once any defects are located, the defect classification system 12 identifies and uses recorded characteristics of defect images stored in the knowledge base 50 to match the located defects to recorded defects in order to determine the type of defect detected. Once the defect type is determined, the defect diagnosis system 14 matches the defect types stored in the knowledge base 50 to a database of known defect causes in order to judge the cause of the defect. After the cause of the defect is predicted, the defect repair system 16 uses information stored in the knowledge base 50 to determine if the PCB can be repaired, and, if the PCB can be repaired, the defect repair system 16 directs the repair of the PCB.

Anomaly Detection/Location System

Figure 2:
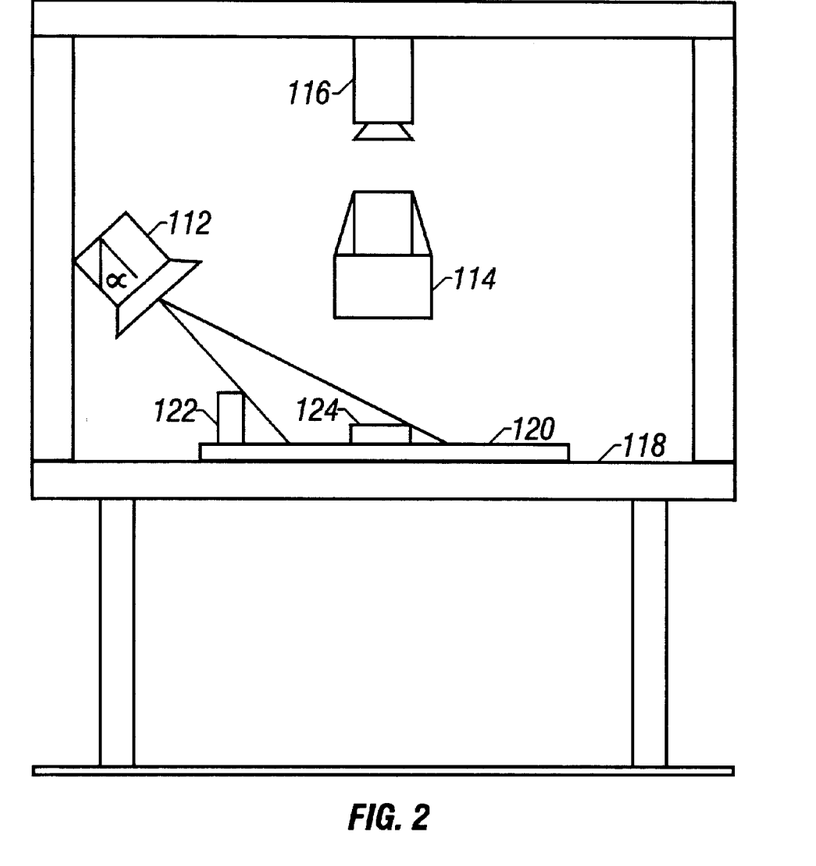
FIG. 2 is a front view of a preferred embodiment of an apparatus according to the present invention.

FIG. 2 is a front view of a preferred embodiment of an apparatus according to the present invention. Shown are the devices used in the anomaly detection/location system 10. The anomaly detection/location system essentially comprises a primary light source 112, a secondary light source 114, an image capturing device 116, and a PCB support 118 which holds PCB 120 having components 122, 124 thereon.

The primary light source 112 and secondary light source 114 are sources which emit light of any visible or non-visible wavelength. The efficiency of the present invention and its ability to detect shadows is largely dependent upon the production of crisp, sharp component shadows. Therefore, both the primary light source 112 and the secondary light source 114 are coherent light sources which minimally diffuse the emitted light, and are mounted at an angle α away from the vertical so as to produce sharply defined shadows from components 122, 124.

The secondary light source 114 should be mounted in such a way as to provide a second set of shadows different from the shadows produced by the primary light source 112. Such shadows can often be created by mounting the secondary source perpendicular to the primary source. But, in any case, the secondary light source location is selected primarily based on the location of the components on the PCB so that the shadows produced by the secondary light source should expose any small components which may go undetected in the shadows of larger components created by the primary light source.

It should be understood that when using only white light sources the primary and secondary light sources are not utilized simultaneously since this would tend to eliminate, or at least soften, the shadows. For example, one method of creating shadows uses strobe lights where the primary light source (a first strobe light) generates a first set of component shadows, turns off, and then the second light source (a second strobe light) produces a second set of component shadows after a minimal delay (typically measured in microseconds).

Alternatively, the primary light source and the secondary light source could produce coherent light in at least two different spectra (wavelengths) such that the primary light source illuminates the PCB with one wave length and the secondary light source illuminates the PCB with another wavelength. If light sources are chosen which illuminate the PCB with light of different wavelengths, the present invention can use a camera which detects the different wavelengths simultaneously (or with two different cameras) so that the PCB shadows produced by the light sources can create shadows simultaneously without creating interference with the shadows created by the other light source. One such method of creating shadows is described for positioning a robot arm in U.S. Pat. No. 4,873,651 to Raviv.

Any angle of the light source less than 90 degrees will produce shadows. However, the angle should be chosen so as to find a balance between the advantage of having easy to detect long shadows and the problem created when longer shadows hide other devices. This angle is usually found between 30 and 60 degrees, the midpoint of which creates a natural default angle of 45 degrees. Occasionally, a PCB will be densely populated with components. In this situation, an angle of less than 30 degrees from the vertical may be necessary to not hide small components in other component shadows. For sparsely populated PCBs, or for PCBs with components of small vertical height, an angle of greater than 60 degrees from the vertical may be preferred in order to generate larger shadows.

The light sources may be adjustable and automated so as to, as much as possible, make an angle of approximately the same measure relative to each image capturing device scan. This could be achieved, for example, by using a line scan camera and placing a PCB on a moving platform that increments the PCB position prior to each line scan pass so as to maintain a constant angle of light against the PCB components at the area being captured by the line scan camera.

The image capturing device 116 is preferably a single line-scan or area-scan overhead camera. One such image capturing device is the XC003 3CCD (Charge Coupled Device) Area-Scan Color Camera available from the Sony Corporation. Accordingly, the present invention particularly detects and measures the lengths of shadows 132, 134 of the components 122, 124 of the PCB 120. Since each component 122, 124 is viewed against that component's shadow cast by a minimally diffused coherent light source, each shadow is "crisp" and each component 122, 124 is easily detected.

Image Decomposition U.S. patent application No. 08/867,156 to YouLing (the parent of the present continuation in part application) discusses a method of image decomposition. The method of image decomposition disclosed by YouLing is briefly discussed below. However, it should be understood that any method of image decomposition can be incorporated into the present invention to produce grammars and gradients, as discussed later.

Figure 3:
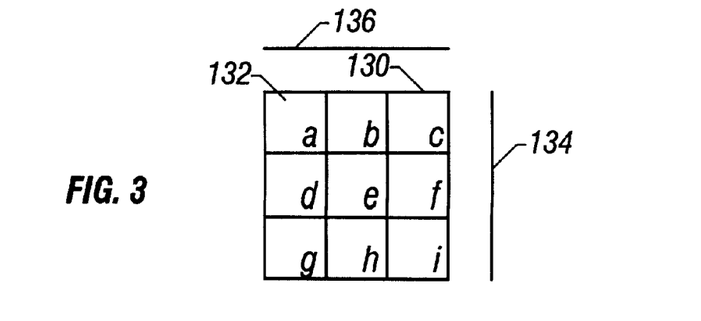
FIG. 3 illustrates a decomposition window of the present invention.

FIG. 3 illustrates a decomposition window 130 of the present invention. The decomposition window 130 comprises a multiplicity of cells 132a–132i (nine cells arranged in a three-by-three matrix). Each cell 132a–132i detects a light intensity of a corresponding pixel and transfers the information to the anomaly detection/location system 10. A cell location in the decomposition window 130, when matched with the information gathered by the other cells in the decomposition window 130, provides the anomaly detection/location system 10 with the information needed to calculate shadow edge locations.

Figure 4:
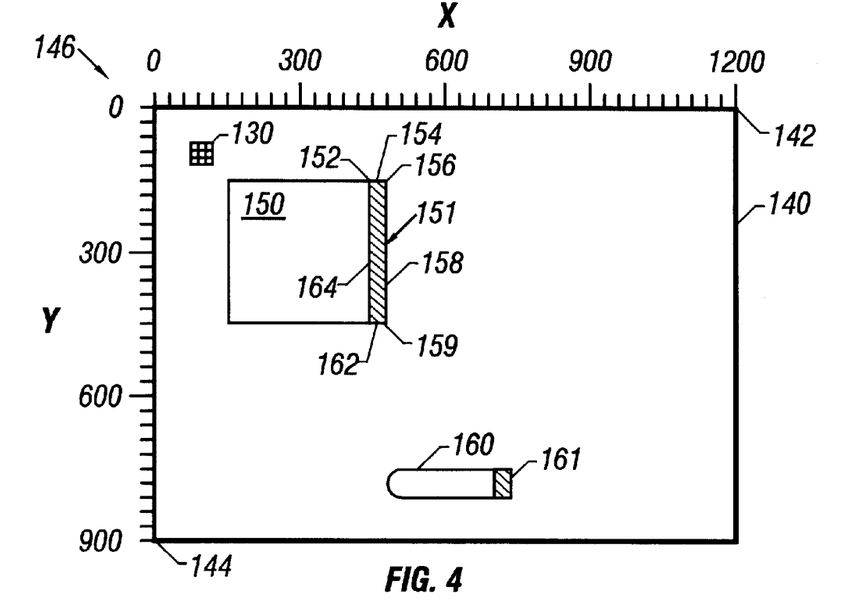
FIG. 4 depicts a captured area of a PCB superimposed upon a grid having a X-axis and a Y-axis.

An image which has been captured by the image capturing device 116 and then digitized by a digitizer (not shown) is referred to as a captured area. FIG. 4 depicts a captured area 140 of a PCB superimposed upon a grid 146 having a X-axis 142 and a Y-axis 144. Each axis 142, 144 has its origin (0 point) in the upper lefthand corner of grid 146, and each point along each axis 142, 144 represents the number of pixels located at that point across that axis in the captured area 140. Here, there are 1200 pixels across the X-axis 142, and 900 pixels down the Y-axis 144. The captured area 140 has a first component 150 having a shadow 151. The shadow 151 has a first corner 152, a first line segment 154, a second corner 156, a second line segment 158, and a third corner 159. Also within captured area 140 is a second component 160 having a shadow 161. Also shown in FIG. 4 is the decomposition window 130.

In operation, an image of a PCB is taken by the image capturing device 116. If the image is an analog image, it is converted into a digital (pixel) format by a digitizer (not shown). Decomposition window 130 has a default search pattern for locating shadows within the captured area 140. Typically the search pattern comprises a series of scans, beginning in one corner of the captured area 140 and proceeding step-wise through the captured area 140 so as to scan the entire captured area 140. For the preferred embodiment, decomposition window 130 begins the series of scans by passing from the upper lefthand corner (0,0) and proceeding in the positive X direction along the X-axis 142 (from left to right for the orientation shown) in pixel increments until the end of the X-axis 142 of the captured area 140 is reached. Next, the decomposition window 130 returns to the left edge of the captured area 140 and increments down the Y-axis 144 by the height 134 of the decomposition window 130 and again begins passing from left to right in the positive X-axis direction. This search pattern is continued until a portion of a shadow or device to be detected is detected by the decomposition window 130. For illustrative purposes, the tracing of a shadow will be discussed.

A shadow is detected by decomposition window 130 when a cell in decomposition window 130 detects a light intensity that indicates an area darker than the lighted bare circuit board has been found. The anomaly detection/location system 10 recognizes the new light intensity as an edge point of a shadow. When a shadow is detected, the decomposition window 130 then traces the shadow (as discussed below) and returns to where the trace began for that particular shadow so it may continue its search according to the previous pattern as if the shadow no longer exists (i.e. the shadow is "masked" and will not be traced a second time). Thereafter, this pattern continues until the entire window is searched or until enough information is gathered to provide an adequate shadow trace.

A primitive is a unit of image information. For a line segment, a common primitive includes a start point, an end point, the light intensity to the left of the line segment, and the light intensity to the right of the line segment. The collection of primitives which completely describes a component, shadow, or a shadow edge is called the item's "grammar." Likewise, a component is said to have a "component grammar," and a shadow is said to have a "shadow grammar."

A grammar allows shadow images to be described in terms of the numeric primitives. For example, a rectangular component produces a rectangular shadow having shadow grammar which articulates coordinates of the corners of the shadow and the light intensity of that shadow in a form such as: [0,0 0,100 100,100 100,0 20] where the commas separate x,y coordinates of shadow corners and the number 20 represents the light intensity detected within the boundary defined by the series of x,y coordinates. Additional primitives which record the shadow area, general shape, position, skew and other characteristics may be used to provide additional definition and more precise shadow descriptions. U.S. Pat. No. 5,515,453 to Hennessey, et al. discusses in detail how a grammar may be generated from primitives or a Computer Aided Drafting (CAD) file, and is hereby incorporated in its entirety by reference.

The construction of a shadow grammar can be understood by way of an illustration that builds shadow grammar for the captured area 140. For purposes of explanation of the preferred embodiment, scanned area 140 has two shadows which will be detected. Upon reaching a first corner 152 of a first component 150 of the captured area 140, decomposition window 130 senses the light intensity of a shadow 151 and begins tracing the shadow 151 in the direction of a first line segment 154, while searching for a change in the light intensity which may signal the end of the first line 154.

Upon reaching a second corner 156, cells in decomposition window 130 indicate or sense a change in the light intensity that match a predetermined threshold which indicates that the end of the line segment 154 has been reached. Thereafter, line segment 154 is considered a single line segment for decomposition purposes. For the line segment 154 the start point is approximately (450, 150) and the end point is approximately (480, 150).

While moving from the start point to the end point, the decomposition window 130 detects and the anomaly detection/location system 10 records the light intensity about the line segment 154. Above (to the left of) line segment 154 a light intensity value of 20 or more will be detected, indicating a lighted PCB or device is detected, below (to the right of) the line segment 154 a light intensity of 5 or less is detected, indicating a shadow area is present. The method of following the line segment is well known in the art. In general, the decomposition window traces a line segment until a change in light intensity is detected by a cell (any cell detects a shadow not previously accounted for, or no longer detects a shadow where one was initially detected).

Upon reaching a corner 156 decomposition window 130 senses a change in light intensity (to the lighted PCB light intensity value, 20), thus signaling an end in line segment 154. The appropriate primitive information for the line segment 154 is then recorded and stored. A trace program directs the movement of the decomposition window around corners. For example, if decomposition window 130 detects a shadow light intensity 5 in cells 132d, 132e, 132g, and 132h, and lighted PCB light intensity 20 in cells 132a, 132b, 132c, 132f, and 132i, the anomaly detection/location system 10 knows that a corner (here, specifically, the second corner 156) has been reached and that the next line segment continues down in the positive Y-axis 144 direction. The decomposition window 130 would then be instructed to continue tracing along the line segment 158 until it detected the next corner 159, where a change in light intensity is again detected and the trace program records the appropriate primitives which describe line segment 158 (the decomposition window 130 is programmed to find and continue tracing the edge of the shadow until the decomposition window 130 again reaches the corner 152 of component 150, where the trace originated).

If no corner is detected within the decomposition window 130, and the decomposition window no longer detects a light intensity, the decomposition window 130, based on preselected programming, may continue along the same path for a predetermined number of steps, here, along the X-axis. Then, if no appropriate light intensity is found within the path, it may retrace its path and search in a direction perpendicular to the initial search path (here, up or down) for the shadow light intensity through predetermined number of Y-axis step. Unless the decomposition window is at the first corner of the trace, the decomposition window should detect a new shadow segment in the search. If at any time the decomposition window 130 is unable to complete a trace of the border of a shadow, it will do as much as possible and then return to where the trace originated and continue the search pattern.

Sometimes, only information regarding one line segment is desired, as in the case of detecting the shadow edge closest to the component (the component-shadow edge, which is also the shadow edge closest to the light source) and so only that edge is traced. At other times it is desired to trace an entire shadow or an entire component. To trace a complete component or shadow, the process continues for each additional line segment. Table 1 lists the information gathered by tracing line segments 154, 158, 162, and 164 of component 150.

TABLE 1

| Primitive | start | end | left | right |
| --- | --- | --- | --- | --- |
| line segment 154 | 450,150 | 480,150 | 20 | 5 |
| line segment 158 | 480,150 | 480,450 | 20 | 5 |
| line segment 162 | 480,450 | 450,450 | 20 | 5 |
| line segment 164 | 450,450 | 450,150 | 20 | 5 |

Figure 5:
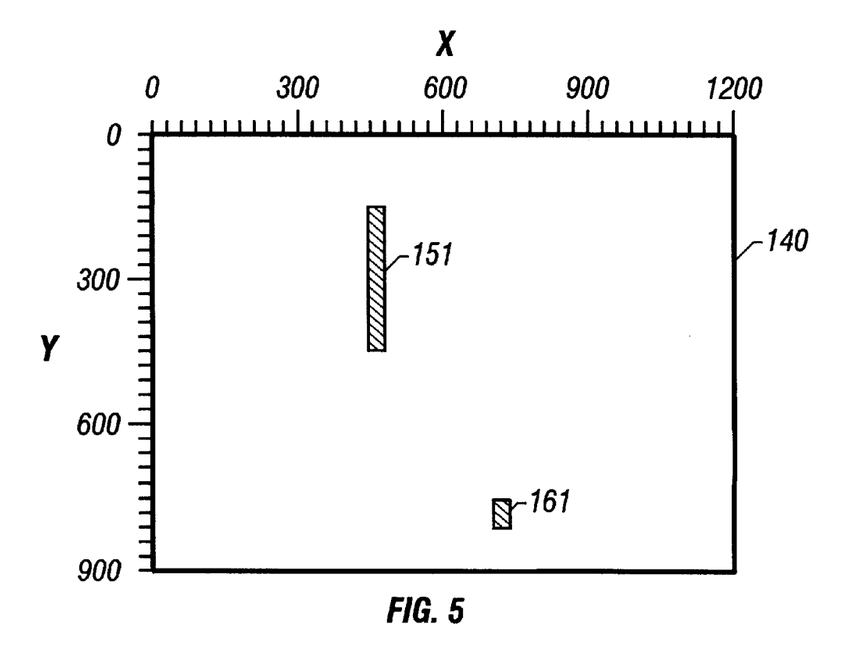
FIG. 5 is an illustration of the captured area of FIG. 4 as reconstructed from primitives stored in the knowledge base, and as seen by the anomaly detection/location system.

Table 1 illustrates how primitives are grouped into sets to create the grammar for the shadow of component 150. FIG. 5 is an illustration of the scanned area 140 as reconstructed from primitives stored in the knowledge base 50, and as seen by the anomaly detection/location system 10.

After having decomposed the line segments into primitives as shown in Table 1, the anomaly detection/location system 10 masks the location of the first shadow edge 151 and begins searching for additional shadow edges where the shadow edge 151 first corner 152 was detected. Thus, having started the trace of shadow edge at corner 152, the decomposition window 130 returns to corner 152 and continues searching for additional shadow edges as described above. Because of masking, the next point that the decomposition window will pick up is a corner of a second shadow edge 161. The anomaly detection/location system will then trace the second shadow edge 161 as described above.

Afterwards, the trace will again continue as described above, eventually terminating at the bottom-right-hand corner of the captured area 140. When the entire shadow edge is traced, the anomaly detection/location system 10 has then produced a grammar for the captured area 140 shadow 151. As previously noted, two light sources in different spectra may be utilized (for example, a red light and a blue light). If one tracing system traces shadow edges created by red light, and another tracing system traces shadow edges created by blue light, multiple shadow edges may be traced simultaneously. It should be understood that device comparisons can be accomplished with as little as a single primitive, such as a line segment.

Image Comparison

The edge of a component shadow can be located by a gradient, which is defined as the change, or difference, between the light intensity of a shadow and the light intensity of a non-shadow area of the PCB. Typically, a gradient is defined across a line, such as a shadow edge. For example, the shadow-component edge gradient is the difference in light intensity between the lighted component and the shadow cast by the component, across the component-shadow edge.

To confirm the presence of shadows, a gradient difference is calculated. A gradient difference is the change in PCB gradient between the production PCB image captured from the first light source, and the production PCB image captured from the second light source. When shadows are present, the shadow edges disappear when switching from the first light source to the second light source. Because the shadow of a first image is not present in the second image, and because the shadow of the second image is not present in the first image, a gradient difference of approximately zero across a scanned area indicates an absence of shadows in the production PCB, whereas measurable differences beyond a predetermined threshold, indicate the presence of shadows.

Figure 6:
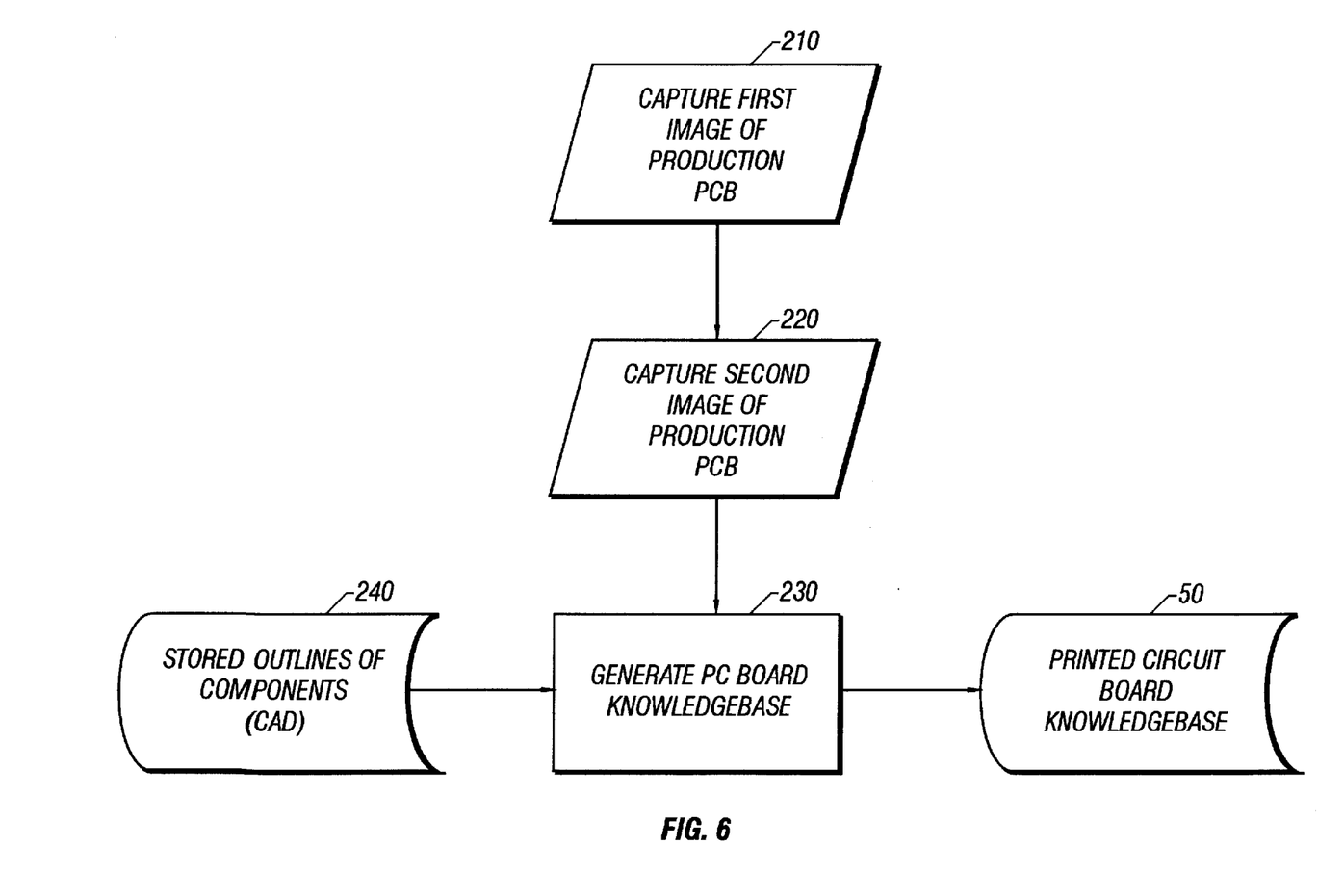
FIG. 6 is a flow chart illustrating an overview of the steps involved in preparing a Printed Circuit Board (PCB) knowledge base in one embodiment of the method of the present invention.

FIG. 6 is a flow chart that illustrates the steps involved in preparing a PCB knowledge base 50 using the PCB anomaly detection/location system 10 of the present invention. FIG. 6 charts the steps of generating PCB shadow edge grammar and component grammar by capturing an image as discussed above in an image capturing step 210, or by constructing PCB shadow edges and component grammar by a CAD device in a CAD grammar step 240. Either process can be used to build the PCB knowledge base 50.

If a component grammar is to be constructed from an image of a defect-free PCB, the primary light source 112 is activated to illuminate the defect-free PCB and cast component shadows on the top surface of the defect-free PCB. An image of the defect-free PCB is captured by the image capturing device 116 in a first image capturing step 210. This provides the anomaly detection/location system 10 with the light values of the unpopulated areas of the defect-free PCB, the light values of the defect-free PCB's components, and the light values of a first set of shadows.

In a second image capturing step 220 the defect-free PCB in the anomaly detection/location system 10 is illuminated by secondary light source 114 which activates to create component shadows so that an image of the properly populated PCB is captured by the image capturing device 116 of the anomaly detection/location system 10. Additional images may be obtained by conducting additional image capturing steps by utilizing additional light sources to cast additional sets of component shadows at different angles. Additionally, if each light source 112, 114 illuminates the PCB with light of different wavelengths, the images produced by the light sources 112, 114 can be captured in a single step by using a camera to detect each wavelength, or by using a single multiple spectra light and color camera, which divides the light frequencies into the desired wavelengths for processing by the anomaly detection/location system 10.

If CAD is used to build PCB grammar, in a CAD step 240, a CAD data file or image is produced. In the PCB knowledge base generation step 230 the captured images or CAD information is used by a computer to produce shadow edge primitives, as discussed in the Image Decomposition section, and then these primitives are organized by component to produce grammars which are stored in the PCB knowledge base 50. The knowledge base 50 stores the image grammar which will be used later by the anomaly location/detection system computer to compare a production PCB gradient to a defect-free PCB gradient to detect PCB defects.

Using the previous values generated in the Image Decomposition section, the lighted area of the PCB's unpopulated captured area 140 has a light intensity value of 20 while the shadow area has a light intensity value of 5. For illustration, assume that the illuminated component has been found to have a light intensity value of 17 when under angular light. To produce shadow edge gradients for the defect-free PCB, the light intensity values of the PCB just outside the shadow (intensity value of 20) generated by the angular primary light source 112 is subtracted from the light intensity values of the shadow area just inside the shadow edge. Thus, the PCB shadow edges would produce a shadow gradient of 15, except at the component-shadow edge where a component-shadow edge gradient of 12 would be produced.

Figure 7:
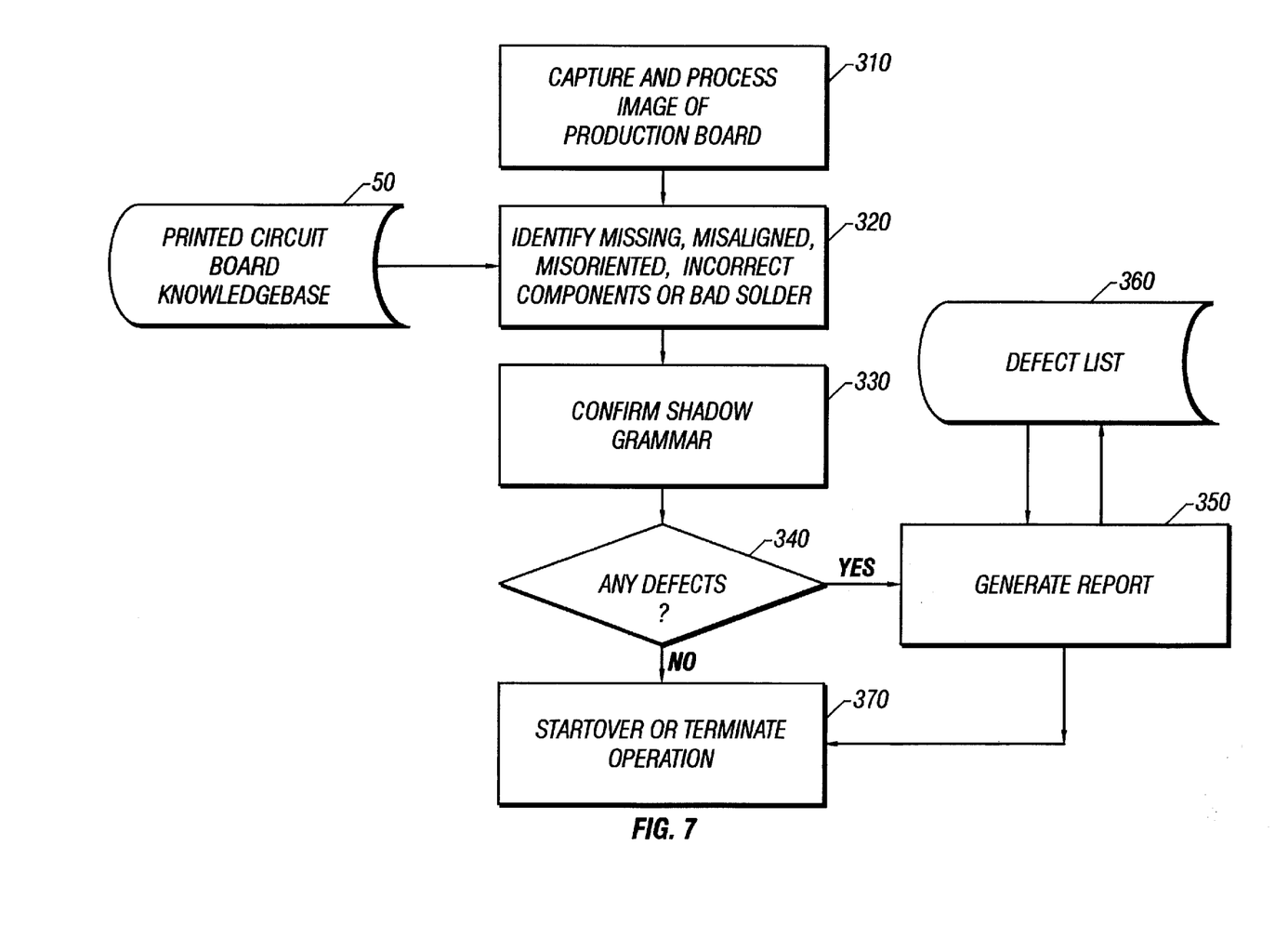
FIG. 7 is a flow chart which depicts an overview of the steps for optically inspecting a PCB for defects in accordance with the teachings of the present invention.

FIG. 7 is a flow chart which depicts the steps for optically inspecting a production PCB for defects in accordance with the teachings of the present invention. A PCB which has undergone manufacturing operations and which is populated with components is placed on a PCB support 118 under an area-scan camera 116. In an image capturing and processing step 310, a primary light source 112 is activated, a first image is captured and shadow grammar is generated therefrom. The image capturing step 310 may optionally include turning on the secondary light source 114 which may be accomplished simultaneously if different wavelengths are used, and using the area-scan camera 116 to capture additional images and generate additional grammars. The grammars are then processed as discussed above to produce shadow edge gradients. If multiple light sources of different wavelengths are used, a multiple spectral light and color camera is used to capture both images simultaneously.

In a comparison step 320 the captured image component-shadow edge gradients and shadow edge gradients generated from the captured image of the production PCB are compared with defect-free PCB component-shadow edge gradients and shadow edge gradients stored in knowledge base 50. Ideally, the difference (numerical) between the production PCB gradients and the defect free PCB gradients will be zero. However, some adjustments can be made to allow for minor detection errors by configuring the system to accept non-zero values (for example, a gradient difference of one) as defect-free.

In a confirmation step 330 the presence of shadows is confirmed by comparing the production PCB image captured from the primary light source to the production PCB image captured from the secondary light source. As discussed above, when shadows are present, the shadow edges disappear when switching from the first light source to the second light source. Therefore, a gradient difference of approximately zero across a scanned area indicates an absence of shadows, whereas a measurable gradient difference beyond a predetermined threshold, indicates the presence of a shadow.

Accordingly, in a defect detection decision step 340 if no defects are detected the method proceeds to a PCB removal step 370. If any defects are detected (if, for example, the difference between the production PCB component-shadow edge gradient and the defect-free PCB component-shadow edge gradient is 12, this indicates that a component is missing), the method proceeds to a report generation step 350. A defect list 360 is a collection of known and possible grammars and gradients that indicate the detection of a PCB defect. In the report generation step 350 the defects that were detected in the image comparison step 320 are then compared to the defect list 360 and a report is generated. In addition, any detected defects not presently in the defect list 360 are added to the defect list 360 for future reference. If defects are detected, following the report generation step 350, a PCB removal step 370 is executed. In the PCB removal step 370, the PCB being evaluated is removed and either another PCB is placed in the system for evaluation or the system operation ends.

Figure 8:
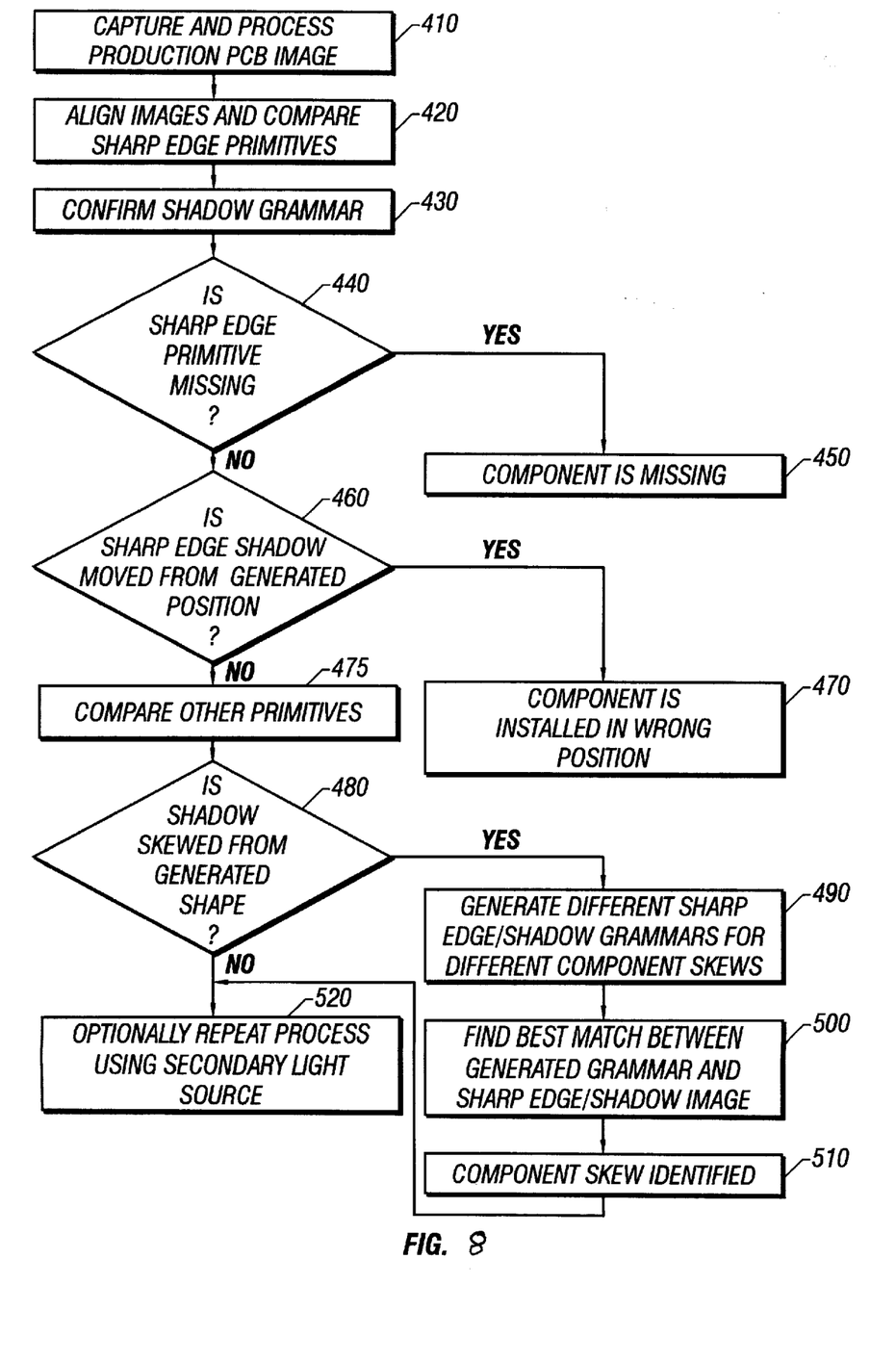
FIG. 8 is a detailed flow chart of the method of the present invention where the production PCB shadow grammar is compared with stored PCB grammar from a properly manufactured and populated PCB.

FIG. 8 is a flow chart of the method of the present invention where the production PCB shadow edge gradients are compared with the stored defect-free PCB shadow edge gradients. For purposes of the present discussion, it is assumed that the PCB knowledge base 50 has been created as discussed and shown in FIG. 6. In a first image capturing and processing step 410 an image of the production PCB is captured as discussed above and shown in FIG. 7. In an alignment step 420, known shadow grammar corresponding to component edges, or specific alignment points on the production PCB, are aligned (matched) with corresponding component edges or specific alignment points for defect-free PCB grammar stored in the knowledge base 50. Aligning can be accomplished based on probability sampling, the method of which is well known in the art. When looking specifically to match shadow edges, the anomaly detection/location system 10 knows where the active light source is located, and thus, knows that the shadow edge next to the component edge (the component-shadow edge) is the shadow edge closest to the active light source. This allows the anomaly detection/location system 10 to gather much information by processing only one set of primitives (the component-shadow edge primitives) to determine several PCB attributes.

A comparison step 430, identical to the comparison step 330, is executed to confirm the presence or absence of shadows. In a component-shadow edge detection step 440 it is determined whether or not correct shadows are present by comparing the component-shadow edge primitive and gradient information of the properly populated PCB to the production PCB's component-shadow edge primitive and gradient information. If the component-shadow edge gradient difference between the defect free PCB and the production PCB is non-zero, the shadow of the component-shadow edge is missing, and thus, it is determined that the component is missing, signified by the component missing decision 450. It is possible that the proper component-shadow edge will be detected in a position other than the position stored in the knowledge base 50. In a component-shadow edge locator step 460 it is determined if the component has been placed in the correct position, and, if not, that fact is reported as indicated by the wrong position decision 470. Because component-shadow edge gradients constitute less data than the entire shadow or PCB gradient, processing component-shadow edge gradient information is much faster than processing the gradient information for a shadow or an entire PCB. Thus, by first comparing component-shadow edge gradients, the system can determine more quickly if a PCB is rejected than if the entire shadow or PCB gradient were compared. If no defects are found by comparing component-shadow edge gradients, the anomaly detection/location system 10 proceeds to compare other primitives of the gradients in a compare other primitives step 475.

If the component-shadow edge has not moved from its correct position, the process moves to a shadow skew detection step 480 where the remainder of the gradients produced from the shadows and components are then compared to the defect-free PCB gradients stored in knowledge base 50.

If a shadow edge is detected and its length is shorter than expected, then the corresponding component is impacted into the PCB, the component is damaged, or an incorrect component is installed. If a shadow edge is detected and its length is longer than expected, then the component is not properly vertically seated, or an incorrect component is installed. If a component-shadow edge is skewed in these or other ways, the process conducts a skew estimation step 490 whereby the component skew is estimated from the gradient of the shadow edges. The skew estimation step is followed by a confirmation step where a grammar is generated for each skew found on the production PCB and compared to the skew grammars stored in the knowledge base 50. Once all skews have been detected, the process executes a matching step 500. In the matching step 500, the detected skewed shadow grammars of the production PCB are compared to a database of skewed grammars stored in the knowledge base 50. When the calculated skew of a component matches that of a stored skew grammar for that component, the process reports the match in a skew identified step 510. Alternatively, if no such match is detected, that fact is also reported in the skew identified step 510.

A method of practicing PCB grammar comparison is described in further detail in U.S. Pat. No. 5,696,836 which issued on Dec. 9, 1997 which is hereby incorporated herein by reference. A method of automated object identification and classification of object anomalies is described in U.S. Pat. No. 6,014,461 which issued on Jan. 11, 2000, entitled "Apparatus and Method for Automatic Knowledge-Based Object Identification", which is hereby incorporated by reference in its entirety. The method discussed creates a pixel map from a captured image and converts the pixel map into primitives. The pixel map and primitives are then converted into a set of high level descriptors based on relevant features such as shape, color, sharpness, and texture. These descriptors are compared to sets of descriptors in a knowledge base to classify the object or anomaly, and to update the knowledge base.

When focusing on shadow detection, the images cast by shadows are typically smaller than the components themselves. Because the shadows are smaller than their components, shadow image tracing is accomplished more quickly than traditional component image processing. Yet faster image processing is achieved by processing shadow edge gradients. Faster image processing leads to a faster throughput which saves the user of the system time and money.

As the present invention detects shadows based on the light being reflected from sections of a PCB, the color of PCBs and devices are now irrelevant. Furthermore, proper vertical seating detection is now possible. Since the length of each component shadow is predetermined, the height of each component is easily determined since components which are not fully seated will have longer than normal shadows and components which are embedded will have shorter than normal shadows. Foreign objects, such as stray drops of solder, will cast shadows where there should not be a shadow, whereas the absence of an expected shadow would indicate a missing component. Because an image capturing device can also capture visible attributes of the PCB, orientation marks can be detected. Thus, the presence or absence of shadows, the offset of shadow edges, the shape of shadows, and the PCB orientation marks provide a complete height image of the PCB and its components.

It is thus believed that the operation and construction of the present invention will be apparent from the foregoing description. While the method, apparatus and system shown and described has been characterized as being preferred, it will be readily apparent that various changes and modifications could be made therein without departing from the spirit and scope of the invention as defined in the following claims.

What is claimed is:

1. A system for inspecting a production printed circuit board (PCB) having a top surface and at least one component mounted thereon, said system comprising:
   a PCB support for supporting the production PCB;
   a first device that emits light at an angle relative to the top surface of the production PCB such that the component casts a first shadow upon the production PCB;
   a second device that emits light at an angle relative to the top surface of the production PCB, wherein the second device emits light of a different wavelength and in a different direction than the first device such that the component casts a second shadow upon the production PCB;
   an image capturing device mounted above the PCB support for simultaneously and separately capturing the first and second shadow images produced by the light-emitting devices; and
   a computer that executes a defect-detection analysis using the captured shadow images.

2. The PCB inspection system of claim 1 wherein the image capturing device is a multiple-CCD camera.

3. The PCB inspection system of claim 1 wherein the computer compares a shadow-edge grammar generated from an image of the production PCB to a corresponding shadow-edge grammar for a defect-free PCB.

4. The PCB inspection system of claim 1 wherein the first device that emits light is a visible spectrum light source.

5. The PCB inspection system of claim 1 wherein the computer comprises a means for processing the captured image of the production PCB to generate shadow edge grammar.

6. The PCB inspection system of claim 1 wherein the computer includes means for comparing a gradient generated for the production PCB to a gradient generated for the defect-free PCB.

7. The PCB inspection system of claim 1, wherein the second device that emits light operates in a different spectrum than the first device that emits light.

8. The PCB inspection system of claim 1, wherein the computer includes means for comparing a gradient for the production PCB generated from the first device that emits light to a gradient for the production PCB generated from the second device that emits light.

9. The PCB inspection system of claim 1, wherein the first device that emits light is mounted to emit light at an angle of less than 90 degrees relative to the PCB.

10. The PCB inspection system of claim 9 wherein the angle of less than 90 degrees is an angle of between 30 degrees and 60 degrees relative to the PCB.

11. The PCB inspection system of claim 9 wherein the angle of less than 90 degrees is an angle of about 45 degrees relative to the PCB.

12. The PCB inspection system of claim 9 wherein the angle of less than 90 degrees is an angle of less than 30 degrees relative to the PCB.

13. The PCB inspection system of claim 3 further comprising a knowledge base accessible by the computer for receiving and storing at least one shadow edge grammar of the defect-free PCB.

14. The PCB inspection system of claim 1 wherein the computer compares a predetermined set of primitives generated from the captured shadow images to a corresponding set of primitives for a defect-free PCB.

15. The PCB inspection system of claim 14 wherein the predetermined selection of primitives includes the primitives for the edges of the first shadow and of the second shadow that are closest to the respective light-emitting device that generated them ("near edges").

16. The PCB inspection system of claim 14 wherein the predetermined selection of primitives includes the primitives for the edges of the first shadow and of the second shadow that are not the near edge of each shadow.

17. The PCB inspection system of claim 1, wherein the first and second devices that emit light are a single light source used in conjunction with a divider that divides the source light into the desired wavelengths that are then separately emitted toward the PCB surface.

18. The PCB inspection system of claim 1, wherein the image capturing device is a camera that separates the reflected light into the component wavelengths corresponding to the wavelengths emitted by the devices that emit light.

19. The PCB inspection system of claim 1, wherein the second device that emits light is mounted at a different angle relative to the surface of the PCB than the first device that emits light.

20. A method of detecting defects on a production printed circuit board (PCB) having a top surface and at least one component mounted thereon, the method comprising the steps of:
    shining a first light on the production PCB at a first angle that generates a first shadow corresponding to the at least one component, said shadow having a first plurality of shadow edges;
    shining a second light that operates at a different wavelength than the first light on the production PCB at a second angle that generates a second shadow corresponding to the at least one component, said shadow having a second plurality of shadow edges;
    capturing an image of the production PCB, the image including the shadows generated by the first light and the second light;
    detecting simultaneously and separately the shadows from the captured image; and
    executing a defect-detection analysis using the captured shadows.

21. The method of claim 20 wherein the step of shining a first light includes shining a light from a light source shining at less than 60 degrees relative to the top surface of the production PCB.

22. The method of claim 20 wherein the second light is in a different spectrum than the first light.

23. The method of claim 20, wherein the defect-detection analysis step includes producing at least one primitive for an edge of the first shadow and for an edge of the second shadow.

24. The method of claim 23, wherein the step of executing a defect-detection analysis includes calculating a shadow-edge gradient difference between the production-PCB image generated by the first light and the production-PCB image generated by the second light.

25. The method of claim 23 further comprising the step of storing the produced primitives in a knowledge base.

26. The method of claim 23, wherein the defect-analysis step further includes comparing a pre-selected set of the produced primitives to a corresponding set of predetermined correct primitives.

27. The method of claim 26 wherein the predetermined correct primitives are produced through computer aided drafting.

28. The method of claim 26, wherein the pre-selected set of primitives includes the primitives for the near edge of each of the shadows.

29. The method of claim 26, wherein the pre-selected set of primitives includes the primitives for at least one non-near edge of each of the shadows.

30. An apparatus for inspecting a production printed circuit board (PCB) comprising:

first means for conveying energy at an angle less than 90 degrees relative to the production PCB such that each PCB component mounted on a top surface of the production PCB casts a shadow upon the production PCB;

second means for conveying energy that conveys energy in a wavelength different than the first means for conveying energy;

means for simultaneously and separately capturing the images for the shadows generated by each means for conveying energy; and means for performing a defect-detection analysis using the captured shadow images.

31. The production PCB inspection apparatus of claim 30 wherein the means for performing a defect-detection analysis includes means for comparing a shadow-edge grammar generated for the production PCB to a corresponding grammar generated for the defect-free PCB in order to detect defects in the production PCB.

32. The apparatus for inspecting a production PCB of claim 30 wherein the means for performing a defect-detection analysis includes means for comparing a gradient for the production PCB generated from the first means for conveying energy to a gradient for the production PCB generated from the second means for conveying energy.

33. The apparatus for inspecting a production PCB of claim 30 wherein the means for performing a defect-detection analysis includes means for calculating a gradient difference.

* * * * *